(12) United States Patent
Kuth et al.

(10) Patent No.: US 10,049,849 B2
(45) Date of Patent: Aug. 14, 2018

(54) MAGNETIC SHIELDING OF AN X-RAY EMITTER

(71) Applicant: Siemens Healthcare GmbH, Erlangen (DE)

(72) Inventors: Rainer Kuth, Hoechstadt (DE); Nils Pickert, Erlangen (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 0 days.

(21) Appl. No.: 15/896,239

(22) Filed: Feb. 14, 2018

(65) Prior Publication Data

US 2018/0174793 A1 Jun. 21, 2018

Related U.S. Application Data

(62) Division of application No. 15/201,678, filed on Jul. 5, 2016.

(30) Foreign Application Priority Data

Jul. 17, 2015 (DE) .................. 10 2015 213 503

(51) Int. Cl.
*H01J 35/16* (2006.01)
*H05G 1/04* (2006.01)
*H01J 9/00* (2006.01)
*A61B 6/00* (2006.01)

(52) U.S. Cl.
CPC ............... *H01J 35/16* (2013.01); *A61B 6/40* (2013.01); *A61B 6/461* (2013.01); *H01J 9/00* (2013.01); *H05G 1/04* (2013.01); *H01J 2235/166* (2013.01)

(58) Field of Classification Search
CPC .. H01J 35/16; H01J 2235/16; H01J 2235/166; H01J 37/16; H01J 2237/026; H01J 2237/06; H01J 2237/08
See application file for complete search history.

(56) References Cited

U.S. PATENT DOCUMENTS

| 5,223,360 A | 6/1993 | Prengel et al. |
| 5,571,991 A | 11/1996 | Highum et al. |
| 5,807,254 A | 9/1998 | Meulenbrugge et al. |
| 6,352,363 B1 | 3/2002 | Munger et al. |

(Continued)

FOREIGN PATENT DOCUMENTS

| CN | 1075390 C | 11/2001 |
| CN | 101636800 A | 1/2010 |

(Continued)

OTHER PUBLICATIONS

German Office Action and English translation thereof dated Apr. 27, 2016.
Chinese Office Action dated Jul. 25, 2017.

*Primary Examiner* — Thomas R Artman
(74) *Attorney, Agent, or Firm* — Harness, Dickey & Pierce, P.L.C.

(57) ABSTRACT

An x-ray emitter includes a housing. In an embodiment, the method for assembling the housing includes producing a housing of the x-ray emitter and assembling the housing. The producing includes providing a material including a plurality of ferromagnetic particles, aligning the ferromagnetic particles through a magnetic field, the material being in a flowable state, and solidifying the material and fixing the alignment of the ferromagnetic particles.

16 Claims, 3 Drawing Sheets

(56) References Cited

U.S. PATENT DOCUMENTS

| | | |
|---|---|---|
| 6,975,895 B1 | 12/2005 | Pelc et al. |
| 6,976,853 B2 | 12/2005 | Goto |
| 7,416,335 B2 | 8/2008 | Munger |
| 7,799,179 B2 * | 9/2010 | Maass .................. C23C 14/351 204/192.12 |
| 8,516,636 B2 | 8/2013 | Gagnon et al. |
| 2002/0153495 A1 | 10/2002 | Kageyama |
| 2003/0008419 A1 | 1/2003 | Hwang et al. |
| 2007/0030958 A1 | 2/2007 | Munger |
| 2007/0188284 A1 | 8/2007 | Dobbs |
| 2009/0209844 A1 | 8/2009 | Gagnon et al. |
| 2012/0121065 A1 | 5/2012 | Rogers et al. |
| 2017/0018393 A1 | 1/2017 | Kuth et al. |

FOREIGN PATENT DOCUMENTS

| | | |
|---|---|---|
| DE | 19901482 A1 | 8/2000 |
| DE | 102011116327 A1 | 4/2013 |

* cited by examiner

MAGNETIC SHIELDING OF AN X-RAY EMITTER

PRIORITY STATEMENT

The present application is a divisional application of and claims priority under 35 U.S.C. § 120/121 to U.S. application Ser. No. 15/201,678, filed on Jul. 5, 2016, which hereby claims priority under 35 U.S.C. § 119 to German patent application number DE 102015213503.9 filed Jul. 17, 2015, the entire contents of each of which are hereby incorporated herein by reference.

FIELD

At least one embodiment of the invention generally relates to an x-ray emitter and/or a method for producing an x-ray emitter.

BACKGROUND

X-ray emitters include an x-ray tube and a housing surrounding the x-ray tube. The x-ray tube itself likewise includes a housing, which is generally embodied as a vacuum housing. Both types of housing typically comprise a soft-magnetic material.

X-ray emitters and especially x-ray tubes are used in a plurality of medical devices, which include, for instance, radiography systems, angiography systems with one or a number of C-arms and computed tomography systems.

The publication DE 19901482 B4 specifies a multiple examination arrangement with a plurality of imaging systems, which are arranged in a room such that a patient lying on a movable patient support couch can be examined in any of the imaging systems without being repositioned, wherein, in addition to a magnetic resonance system with actively shielded magnets, provision is made for an x-ray angiography system with a soft-magnetic casing in the region of the imaging parts for shielding the static stray field of the magnetic resonance system, and the masses of the soft-magnetic casing on the x-ray angiography system are arranged distributed in symmetry with the axis of rotation thereof.

X-ray tubes are sensitive to magnetic fields because the electrons released in the x-ray tube are electrically charged and can be deflected from their path by magnetic fields. Fluctuating magnetic fields which are affected by fluctuations in the magnetic fields themselves or by movement of the x-ray tube through static or dynamic inhomogeneous fields result in a movement of the focal point of the x-ray tube. The movement of the focal point causes the resolution of the x-ray system to deteriorate.

Moreover, magnetic fields emanating from the x-ray emitter, for instance the magnetic field of the anode drive, can also produce interferences in the surrounding objects, for instance EKG cables.

With current soft-magnetic, almost single crystal housings, a definition of the direction of magnetic flux lines through housing walls is not possible.

SUMMARY

Embodiments of the invention are directed to an x-ray emitter, a medical device and a method for producing an x-ray emitter, which allow the influence of, for instance fluctuating, magnetic fields on the x-ray tube and/or surrounding objects to be reduced.

Embodiments relate to an x-ray emitter, a medical device and a method for producing an x-ray emitter.

An embodiment of the invention relates to an x-ray emitter which has a housing, wherein the housing has a diamagnetic or paramagnetic housing material and also a plurality of ferromagnetic particles and wherein the ferromagnetic particles are aligned substantially along closed paths.

At least one embodiment of the invention further relates to a medical device, which has an x-ray emitter of at least one embodiment.

At least one embodiment of the invention further relates to a method for producing an inventive x-ray emitter, wherein the method comprises: In a step I the housing is produced. In a further step II the housing is assembled. Step I comprises the following steps: In step a, a material is provided which has a plurality of ferromagnetic particles. In a further step b, the ferromagnetic particles are aligned through a magnetic field, wherein during the alignment the material is in a flowable state. And in a further step c, the material is solidified and the alignment of the ferromagnetic particles is fixed. In step II, the housing can be assembled, for instance, as a vacuum housing of the x-ray tube, as an emitter housing, as a housing for the disc motor or as a housing for further components or subregions of the x-ray emitter.

BRIEF DESCRIPTION OF THE DRAWINGS

Example embodiments of the invention are explained in more detail below with the aid of drawings, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

An embodiment of the invention relates to an x-ray emitter which has a housing, wherein the housing has a diamagnetic or paramagnetic housing material and also a plurality of ferromagnetic particles and wherein the ferromagnetic particles are aligned substantially along closed paths.

The housing can be embodied, for instance, as a vacuum housing of the x-ray tube, as an emitter housing, as a housing for the disc motor or as a housing for further components or subregions of the x-ray emitter.

The housing can be embodied in single-part, multi-part, spherical, cylindrical or also in any other, also more complex forms. The housing can have e.g. terminals, recesses, openings, indentations or elevations, for instance cooling ribs.

Glasses or thermoplasts can be used as housing material for instance. The use of a diamagnetic or paramagnetic housing material is advantageous in that in respect of the magnetic properties they differ significantly from ferromagnetic materials. Paramagnetic housing materials can preferably be used.

The ferromagnetic particles can have elements which form ferromagnetic grids, for instance iron, nickel, cobalt or others. Furthermore, the ferromagnetic particles can be alloys, for instance Heusler alloys, or chemical compounds with ferromagnetic properties, magnetite $Fe_2O_3$ for instance.

The ferromagnetic particles can be soft-magnetic, so that the Curie temperature is lower than the temperature before, during or after use of the x-ray emitter.

The ferromagnetic particles can be produced using methods such as machining or crystallization. The form of the ferromagnetic particles can be embodied as a stretched form or as an isotropic form. The dimensions of the ferromagnetic particles lie in the range of 10 to 1000 nm.

The ferromagnetic particles are surrounded by the diamagnetic or paramagnetic housing material. The definition of the direction of the ferromagnetic particles allows for a definition of the directions of magnetic flux lines through the housing wall. The influence of the paramagnetic or diamagnetic housing material on the definition of the directions of magnetic fields is low. The advantage results from the combination of a paramagnetic or diamagnetic housing material with ferromagnetic particles. It is advantageous that by defining the directions of magnetic flux lines through housing walls a shielding effect is achieved with minimal cost of materials.

The alignment of the ferromagnetic particles takes place substantially along closed paths, wherein the ferromagnetic particles may have gaps in respect of the ferromagnetic particles which are adjacent in all three spatial directions. The closed paths lie in parallel to the magnetic flux lines of the magnetic field to be shielded or the closed paths are aligned such that the desired shielding effect can be achieved. The alignment of the ferromagnetic particles can preferably take place with an accuracy of +/−40°, particularly preferably with an accuracy of +/−20° and especially preferably with an accuracy of +/−10°.

In one advantageous variant, particles with an anisotropic form are preferably used. Such particles can be magnetized to form a higher magnetic torque. This results in higher attraction forces in magnetic leakage fluxes and the particles can preferably be selected or aligned.

By defining the magnetic flux lines through the housing, the penetration of magnetic flux lines into the housing volume or the leaving of magnetic flux lines from the housing volume can advantageously be prevented. By defining the magnetic flux lines through the housing, the advantage can be achieved for instance that the electron beam is shielded from external magnetic fields and a deviation from its target path is reduced or avoided.

The distribution of the ferromagnetic particles can take place uniformly in the paramagnetic or diamagnetic housing material. In a further embodiment, the distribution can vary radially, axially, lengthways or widthways for instance.

At least one embodiment of the invention further relates to a medical device, which has an x-ray emitter of at least one embodiment.

The medical device may represent a radiography system, an angiography system with one or a number of C-arms or a computed tomography device for instance.

By defining the magnetic flux lines through the housing, the advantage can be achieved for instance that the electron beam is shielded from external magnetic fields and a deviation from its target path is reduced.

As a result, an improvement in the image resolution for the medical device can advantageously be achieved. Moreover, magnetic fields which emanate from the x-ray emitter itself, for instance from the anode drive, can be advantageously shielded so that the influence of the magnetic field on other components, in other words the interference emission of the x-ray emitter itself, in the surroundings of the x-ray emitter is reduced or avoided. For instance, the induction in EKG cables can be reduced and the advantage that the interference of EKG signals is reduced is thus achieved. The interference emission of the x-ray emitter may lie in the same order of magnitude or also above the signals to be examined, in terms of electrophysiology for instance. The treatment and diagnostic efficiency of other devices such as for instance EKG devices is advantageously improved by shielding the x-ray emitter or one of its components using the housing.

At least one embodiment of the invention further relates to a method for producing an inventive x-ray emitter, wherein the method comprises: In a step I the housing is produced. In a further step II the housing is assembled. Step I comprises the following steps: In step a, a material is provided which has a plurality of ferromagnetic particles. In a further step b, the ferromagnetic particles are aligned through a magnetic field, wherein during the alignment the material is in a flowable state. And in a further step c, the material is solidified and the alignment of the ferromagnetic particles is fixed. In step II, the housing can be assembled, for instance, as a vacuum housing of the x-ray tube, as an emitter housing, as a housing for the disc motor or as a housing for further components or subregions of the x-ray emitter.

The material has the paramagnetic or diamagnetic housing material as well as a plurality of ferromagnetic particles. During the alignment of the ferromagnetic particles, the material is in a flowable state. In the flowable state, the material may be present in fluid, granulate or powder form for instance. In the flowable state, the ferromagnetic particles can advantageously be moved within the material. Advantageously in the flowable state the ferromagnetic particles can be aligned through a magnetic field. The alignment is advantageously fixed by the subsequent solidification thereby permanently ensuring a definition of the alignment within the housing material.

Magnetic fields of one or a number of coils and/or permanent magnets can be used to align the ferromagnetic particles.

The ferromagnetic particles can be embodied in an elongated or stretched form. The dimensions of the ferromagnetic particles lie in the range of 10 to 1000 nm. The longitudinal axis of the ferromagnetic particles can be advantageously aligned substantially in parallel to the magnetic flux lines.

If a magnetic flux is now applied during the solidification, the particles align themselves in parallel in their longitudinal direction. This alignment is fixed during solidification. The direction of the magnetic flux is thus also determined. The magnetic flux through this structure is defined, as a result of which the shielding effect can be anisotropically determined for each volume element.

According to one embodiment of an inventive x-ray emitter, the ferromagnetic particles are elongated.

The form of the ferromagnetic particles can be embodied as a stretched form, for instance in the form of a needle. The dimensions of the ferromagnetic particles lie in the range of 10 to 1000 nm. The elongated ferromagnetic particles can be advantageously aligned within the magnetic field.

According to one embodiment of an inventive x-ray emitter, the ferromagnetic particles are ferromagnetic nanoparticles.

The dimensions of the ferromagnetic particles can lie in the range of 1 to 100 nm. Advantageously a uniform distribution in the housing and thus a uniform shielding can be achieved. Moreover, the small dimensions also advantageously enable complex forms for the housing and the alignment through a magnetic field is simplified.

According to one embodiment of an inventive x-ray emitter, the concentration of the ferromagnetic particles varies.

The concentration of the ferromagnetic particles can advantageously vary radially, axially, lengthways or widthways in order to achieve an optimal shielding effect.

According to one embodiment of an inventive x-ray emitter, the housing surrounds the x-ray tube and/or a disc motor of the x-ray tube.

The housing can surround the x-ray tube. The housing can be the housing of the x-ray emitter for instance. The housing can be oil-filled for instance. It is advantageous that the housing does not need to be vacuum-tight for instance. Advantageously the entire x-ray tube is surrounded by the housing, and a shielding of the entire x-ray tube can be achieved.

The housing can surround the disc motor and particularly advantageously be designed for the magnetic field emanating from the anode drive. Components in the surroundings of the anode drive, for instance for recording an EKG, can be particularly effectively protected from the influence of the magnetic field.

According to one embodiment of an inventive x-ray emitter, the housing material has glass or plastic.

Glass and plastic advantageously allow for particularly good properties in respect of forming the housing and also in respect of mixing the ferromagnetic particles and the housing material.

According to one embodiment of an inventive x-ray emitter, the housing is a vacuum housing.

The housing can represent a vacuum housing and thus also the housing of the x-ray tube. It is advantageous that the vacuum housing having a plurality of ferromagnetic particles can have the additional property that the electron current trajectory is shielded from external magnetic fields. The advantage can thus be achieved that the influence of a for instance fluctuating magnetic field on the focal point is reduced or prevented. At the same time, a minimal cost of materials is achieved by mixing the ferromagnetic particles with the housing material while at the same time having the additional function of a magnetic shielding.

According to one embodiment of an inventive x-ray emitter, the paths run substantially in parallel to magnetic flux lines of a magnetic field to be shielded.

By aligning the ferromagnetic particles along paths which run substantially in parallel to magnetic flux lines of a magnetic field to be shielded, the shielding can be advantageously attuned to the magnetic field to be shielded. An optimal shielding can thus be achieved.

According to one embodiment of an inventive x-ray emitter, the paths run substantially in a plane perpendicular to an electron current trajectory of the x-ray tube.

By aligning the ferromagnetic particles along paths which run substantially on paths perpendicular to the electron current trajectory, the shielding can be advantageously designed in order to shield the accelerated electrons as effectively as possible from influences from external, for instance fluctuating, magnetic fields. With spherical housings, the paths can be aligned in particular in parallel to the lines of latitude of the housing about the electron current trajectory.

According to one embodiment of the inventive method, the housing material is solidified section-by-section.

The section-by-section solidification advantageously serves to achieve a fixing of the alignment of the ferromagnetic particles after alignment of the ferromagnetic particles. Subsequently further material can be provided, and an alignment of the ferromagnetic particles and a subsequent fixing can take place. Production is advantageously simplified by an alignment and fixing of the ferromagnetic particles having to take place at the same time in just one restricted part of the housing. Moreover, the magnetic fields used for alignment can advantageously be aligned individually for each section.

According to one embodiment of the inventive method, the production of the housing comprises the use of a 3D printing method.

The use of a 3D printing method advantageously allows for complex forms of the housing and a particular flexibility in respect of adjustment to different housing types or requirements in respect of the magnetic field to be shielded. The flexibility in respect of the alignment of the ferromagnetic particles is particularly advantageous with the use of 3D printing methods.

According to one embodiment of the inventive method, the alignment of the ferromagnetic particles takes place by applying a substantially homogeneous magnetic field.

A uniform alignment of the ferromagnetic particles can be achieved by using substantially homogeneous magnetic fields. In particular, the parallel alignment of the particles with one another is advantageous under the influence of substantially homogeneous magnetic fields. The alignment of the ferromagnetic particles can be programmed and can be achieved with the aid of a controller of the magnetic field, for instance by controlling the coils.

According to one embodiment of the inventive method, the ferromagnetic particles are aligned by applying a superimposed variable magnetic flux gradient.

By applying a superimposed changeable or variable magnetic flux gradient, the concentration of the ferromagnetic particles in the housing can be varied radially, axially, lengthways or widthways for instance. An optimal shielding effect can advantageously be achieved by varying the concentration. Coils can be used in particular to generate a superimposed variable magnetic flux gradient. By controlling the coils, the magnetic fields generated can vary in time and in intensity for instance. By varying the magnetic flux gradient, a variable tensile force is exerted in the direction of the housing located in the structure, so that a variation of the concentration of the ferromagnetic particles in the housing is achieved. The variation of the concentration can be programmed and can be achieved with the aid of the controller of the magnetic field, for instance by controlling the coils.

Figure 1:
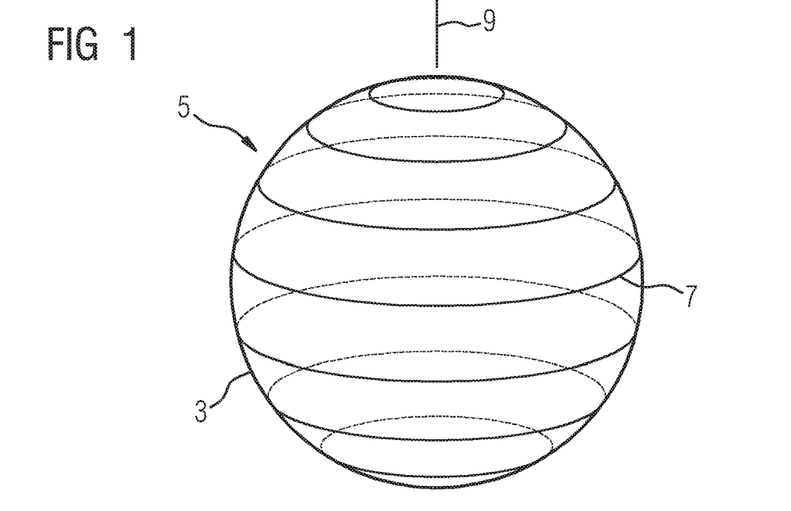
FIG. 1 shows a schematic representation of a spherical housing of an x-ray tube.

FIG. 1 shows an example embodiment of a schematic representation of a spherical housing 3 of an x-ray tube 5. The x-ray tube 5 comprises an anode, for instance a rotating anode or fixed anode, and a cathode (not shown). Further components, for instance anode drive, feedthroughs and terminals may be present. Moreover, protrusions and/or notches may be present on the spherical surface in order to feed in and/or accommodate other components. The electrons emitted by the cathode are accelerated along an electron current trajectory toward the anode. The electron current trajectory is aligned in parallel with the direction of the electron current trajectory 9 specified in the figure. The ferromagnetic particles are aligned along closed paths 7, which run substantially in a plane perpendicular to the direction of the electron current trajectory 9. Paths 7 which are arranged according to the lines of latitude on a spherical surface emerge for the spherical housing 3.

The ferromagnetic particles do not generally form an end-to-end arrangement; they are instead distributed substantially uniformly in the housing 3, wherein the alignment of their longitudinal axis for instance is defined. The accelerated electrons generate a magnetic field in accordance with the Biot-Savart law, a fluctuating magnetic field in the case of the generation of pulsed radiation by way of generator or grid pulsing for instance. Aligning the ferromagnetic particles prevents the magnetic flux lines from leaving the housing 3. Moreover, a penetration of magnetic flux lines of external magnetic fields into the volume of the housing 3 is also prevented.

Figure 2:
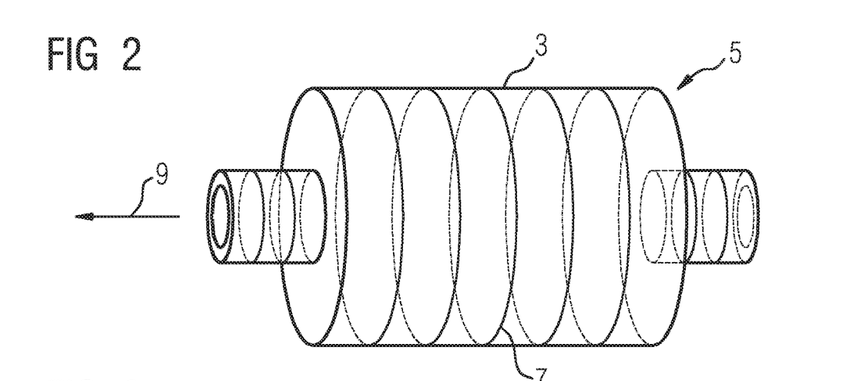
FIG. 2 shows a schematic representation of a cylindrical housing of an x-ray tube.

FIG. 2 shows an example embodiment of a schematic representation of a cylindrical housing 3 of an x-ray tube 5. The cylindrical housing 3 comprises a cylindrical larger volume and cylindrical smaller volumes connected thereto on both top sides, wherein their axis of symmetry coincides with the axis of symmetry of the larger volume. The x-ray tube 5 comprises an anode, for instance a rotating anode or fixed anode, and a cathode (not shown). Further components, for instance anode drive, feedthroughs and terminals may be present.

The electrons emitted by the cathode are accelerated along an electron current trajectory toward the anode. The electron current trajectory is aligned in parallel with the direction of the electron current trajectory 9 along the cylinder axis specified in the figure. The ferromagnetic particles are aligned along closed paths 7, which run substantially in a plane perpendicular to the direction of the electron current trajectory 9. Paths 7 which run along the periphery of the cylindrical volume emerge for the cylindrical housing 3. Circular paths 7 emerge on the top sides.

The ferromagnetic particles do not generally form an end-to-end arrangement; they are instead distributed substantially uniformly in the housing 3, wherein the alignment of their longitudinal axis for instance is defined. The accelerated electrons generate a magnetic field in accordance with the Biot-Savart law, a fluctuating magnetic field in the case of the generation of pulsed radiation by way of generator or grid pulsing for instance. Aligning the ferromagnetic particles prevents the magnetic flux lines from leaving the housing 3. Moreover, a penetration of magnetic flux lines of external magnetic fields into the volume of the housing 3 is also prevented.

Figure 3:
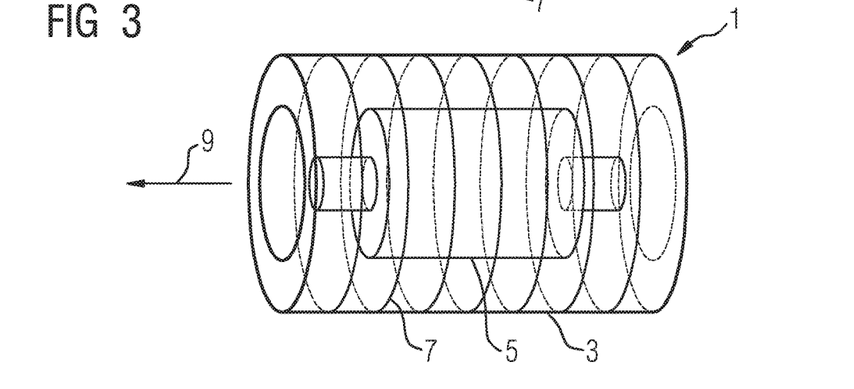
FIG. 3 shows a schematic representation of a cylindrical housing of an x-ray emitter.

FIG. 3 shows an example embodiment of a schematic representation of a cylindrical housing 3 of an x-ray emitter 1. The x-ray emitter 1 comprises an x-ray rube 5 and a cylindrical housing 3. Further components, for instance anode drive, feedthroughs and terminals may be present. The electrons emitted by the cathode are accelerated along an electron current trajectory toward the anode. The electron current trajectory is aligned in parallel with the direction of the electron current trajectory 9 specified in the figure.

The ferromagnetic particles are aligned along closed paths 7, which run substantially in a plane perpendicular to the direction of the electron current trajectory 9. The ferromagnetic particles do not generally form an end-to-end arrangement; they are instead distributed substantially uniformly in the housing 3, wherein the alignment of their longitudinal axis for instance is defined.

Paths 7 which run along the periphery of the cylindrical volume emerge for the cylindrical housing 3. Circular paths 7 emerge on the top sides. The accelerated electrons generate a magnetic field in accordance with the Biot-Savart law, a fluctuating magnetic field in the case of the generation of pulsed radiation by way of generator or grid pulsing for instance. Moreover, the anode drive can generate a further magnetic field. Aligning the ferromagnetic particles prevents the magnetic flux lines from leaving the housing 3. Moreover, a penetration of magnetic flux lines of external magnetic fields into the volume of the housing 3 is also prevented.

Figure 4:
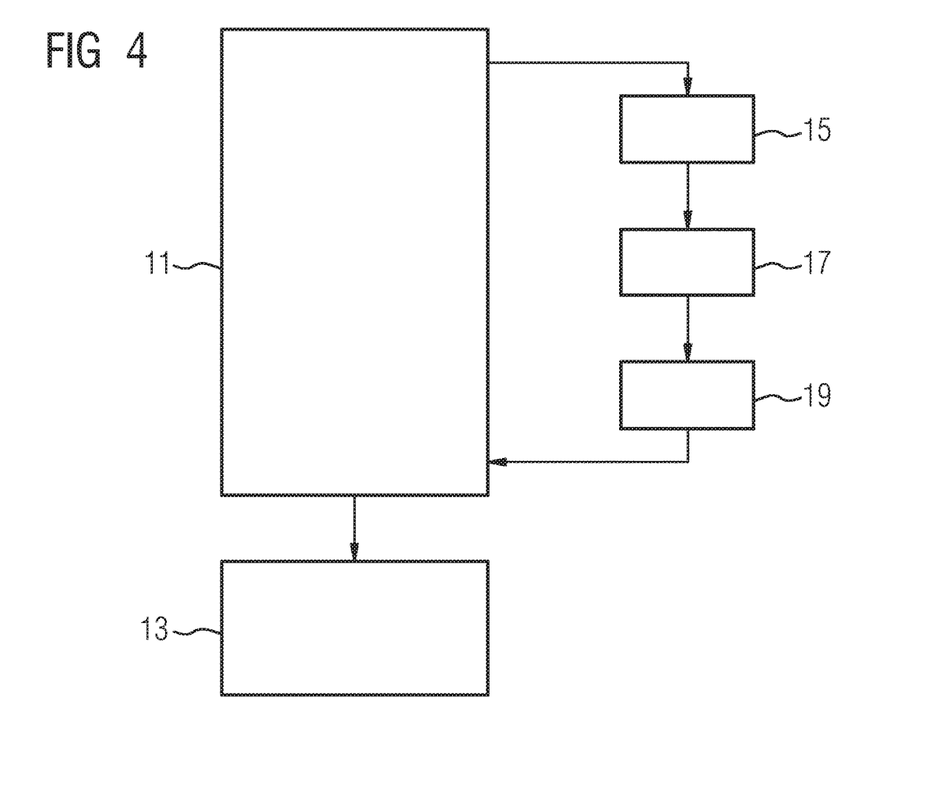
FIG. 4 shows a schematic representation of an embodiment of an inventive method for producing an x-ray emitter.

FIG. 4 shows an example embodiment of an inventive method for producing an x-ray emitter 1. In a first step 11 the housing 3 is produced. In a second step 13 the housing 3 is assembled. Here step 11 has the steps 15, 17 and 19. In step 15, a material having a plurality of ferromagnetic particles is provided. The material is diamagnetic or paramagnetic and may be a plastic, for instance a thermoplast or a glass.

The ferromagnetic particles can have elements which form ferromagnetic grids, for instance iron, nickel, cobalt or others. Furthermore, the ferromagnetic particles can be alloys, for instance Heusler alloys, or chemical compounds with ferromagnetic properties, magnetite $Fe_2O_3$ for instance. The ferromagnetic particles may be present in elongated form, for instance as blades.

In step 17, the ferromagnetic particles are aligned through a magnetic field, wherein during the alignment the material is in a flowable state. A flowable state may be present by way of a liquid, a granulate or a powder for instance. In step 19, the material is solidified and the alignment of the ferromagnetic particles is fixed. The solidification can take place section-by-section. The solidification can take place by way of cooling, sintering or pressing for instance. The alignment of the ferromagnetic particles is permanently defined by the solidification of the material. The housing has what is known as a magnetic texture.

Figure 5:
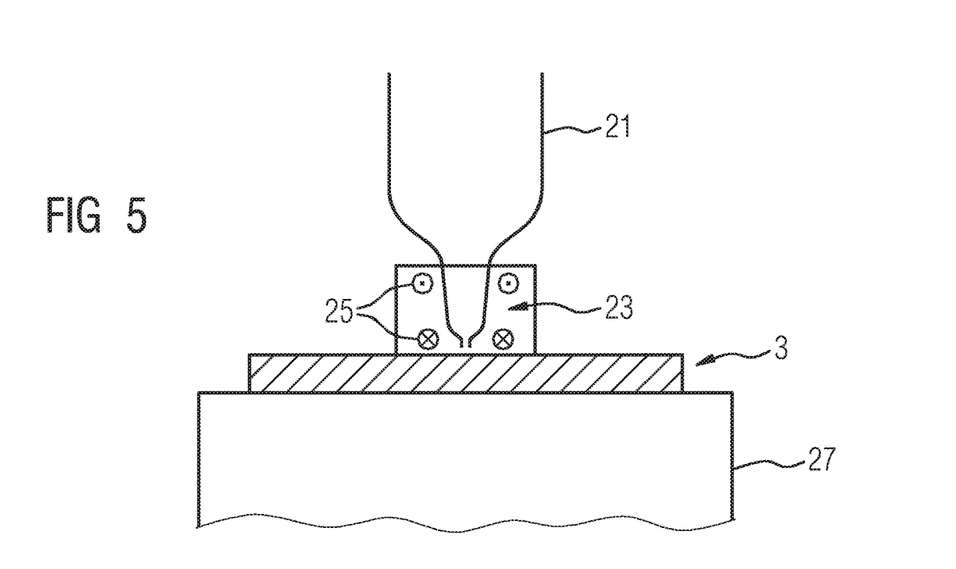
FIG. 5 shows a schematic representation of an apparatus for aligning the ferromagnetic particles while producing an x-ray emitter by way of 3D printing methods.

FIG. 5 shows an example embodiment of an apparatus for the inventive production of a housing 3 by way of a 3D printing method. The material having a plurality of ferromagnetic particles is provided in a funnel-shaped container 21. The pressure nozzle 23 has coils 25 for generating a substantially homogeneous magnetic field. The ferromagnetic particles are aligned in the material under the influence of the substantially homogeneous magnetic field, wherein the material is in a flowable state. The material is placed on a pressure platform 29, the material is solidified and in this way the alignment of the ferromagnetic particles is fixed. The housing 3 is produced using a 3D printing method. The material is solidified section-by-section.

Figure 6:
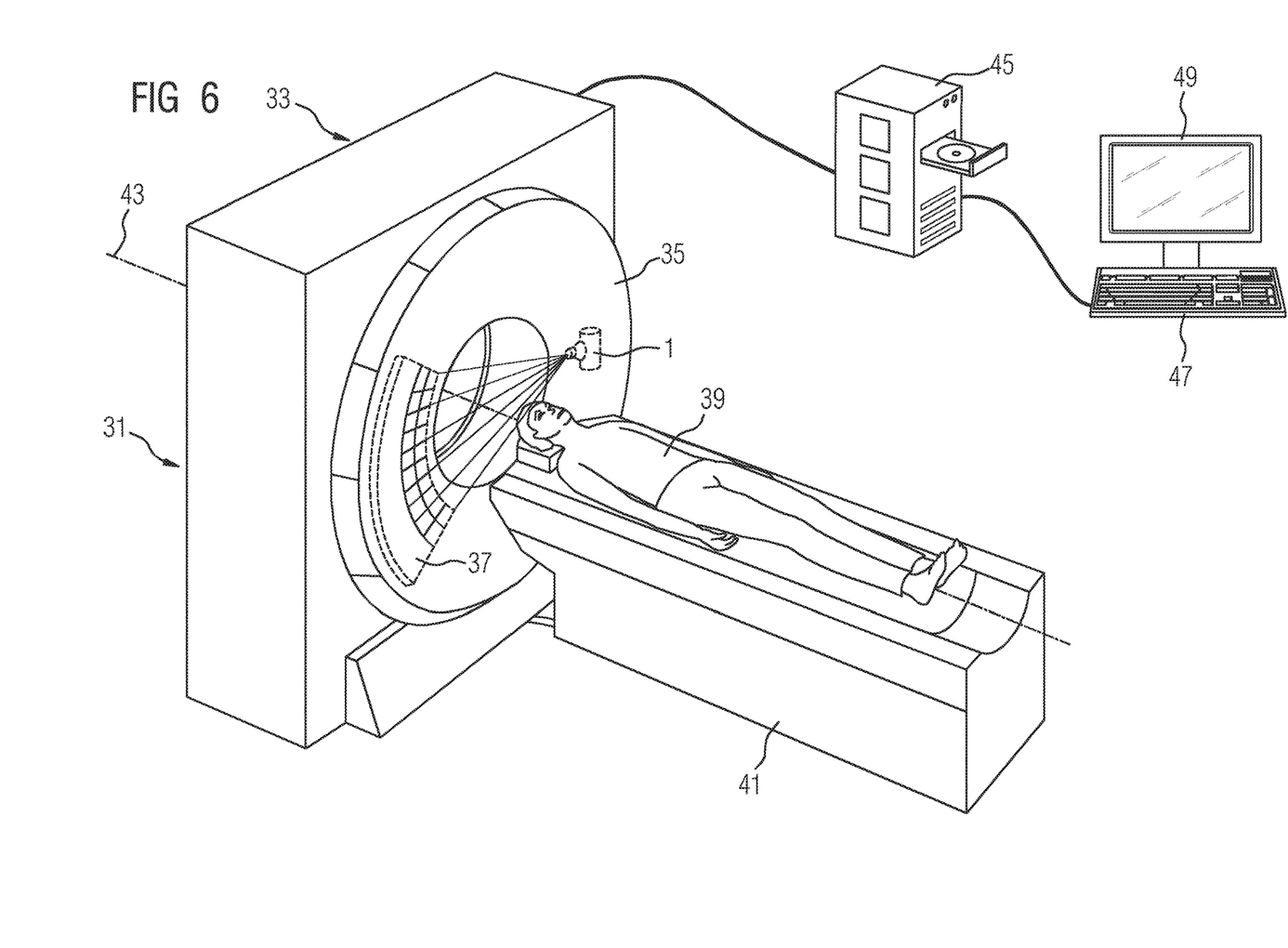
FIG. 6 shows a schematic representation of a computed tomography system with an embodiment of an inventive x-ray emitter.

FIG. 6 shows a computed tomography system 31 with an inventive x-ray emitter 1. The computed tomography system 31 contains a gantry 33 with a rotor 35. The rotor 35 comprises an x-ray emitter 1 and a detector apparatus 37. The patient 39 is supported on the patient couch 41 and can be moved along the axis of rotation z 43 through the gantry 33. A computing unit 45 is used to control and calculate the cross-sectional images. An input facility 47 and an output apparatus 49 are connected to the computing unit 45. By aligning the ferromagnetic particles in the housing, the influence by the movement of the gantry 33 and thus also of the x-ray emitter 1 through static or dynamic inhomogeneous fields and/or through the fluctuation of the magnetic fields is reduced or prevented. An improved resolution is achieved. Moreover, the interference emission of the x-ray emitter 1 itself in the surroundings of the x-ray emitter 1 can be reduced or avoided. For instance, the induction in EKG cables (not shown) can be reduced or prevented and the advantage that the interference of EKG signals is reduced is thus achieved.

Although the invention has been illustrated in greater detail by the preferred example embodiment, the invention is not limited by the examples disclosed and the person skilled in the art will be able to derive other variations on this basis without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for assembling a housing of an x-ray emitter comprising:
   producing a housing of the x-ray emitter, the producing including
     providing a material including a plurality of ferromagnetic particles,
     aligning the ferromagnetic particles through a magnetic field, the material being in a flowable state, and
     solidifying the material and fixing the alignment of the ferromagnetic particles; and
   assembling the housing.

2. The method of claim 1, wherein the solidifying of the material takes place section-by-section.

3. The method of claim 1, wherein the producing of the housing includes using a 3D printing method.

4. The method of claim 1, wherein the aligning of the ferromagnetic particles take place by applying a substantially homogeneous magnetic field.

5. The method of claim 1, wherein the aligning of the ferromagnetic particles take place by applying a superimposed variable magnetic flux gradient.

6. The method of claim 2, wherein the producing of the housing includes using a 3D printing method.

7. The method of claim 2, wherein the aligning of the ferromagnetic particles take place by applying a substantially homogeneous magnetic field.

8. The method of claim 3, wherein the aligning of the ferromagnetic particles take place by applying a substantially homogeneous magnetic field.

9. The method of claim 2, wherein the aligning of the ferromagnetic particles take place by applying a superimposed variable magnetic flux gradient.

10. The method of claim 3, wherein the aligning of the ferromagnetic particles take place by applying a superimposed variable magnetic flux gradient.

11. The method of claim 1, wherein the material provided for the housing includes a diamagnetic or paramagnetic housing material and the plurality of ferromagnetic particles.

12. The method of claim 1, wherein the plurality of ferromagnetic particles are aligned substantially along closed paths.

13. The method of claim 11, wherein the plurality of ferromagnetic particles are aligned substantially along closed paths.

14. The method of claim 1, wherein the ferromagnetic particles are elongated.

15. The method of claim 1, wherein the ferromagnetic particles are ferromagnetic nanoparticles.

16. The method of claim 15, wherein a concentration of ferromagnetic particles varies.

* * * * *